United States Patent [19]

McAuley

[11] Patent Number: 5,087,695

[45] Date of Patent: Feb. 11, 1992

[54] IMMUNOGLOBULIN EXTRACTION UTILIZING PROPERTIES OF COLLOIDAL SOLUTIONS

[75] Inventor: William A. J. McAuley, Portland Township, Frontenac County, Canada

[73] Assignee: MCY Laboratories Canada, Inc., Canada

[21] Appl. No.: 378,975

[22] Filed: Jul. 12, 1989

[30] Foreign Application Priority Data

Jul. 29, 1988 [CA] Canada .................................. 573360

[51] Int. Cl.$^5$ ........................ C07K 3/24; A61K 37/04
[52] U.S. Cl. .................................... 530/387; 530/412; 530/418; 530/419; 530/420; 424/85.8
[58] Field of Search ............... 530/387, 419, 412, 418, 530/420; 424/85.8

[56] References Cited

U.S. PATENT DOCUMENTS

| | | | |
|---|---|---|---|
| 3,549,610 | 12/1970 | Yamamoto et al. | 530/419 |
| 3,701,768 | 10/1972 | Fortini et al. | 530/419 |
| 3,808,189 | 4/1974 | Breuer | 530/387 |
| 4,256,631 | 3/1981 | Yokoo et al. | 530/387 |
| 4,486,282 | 12/1984 | Bier | 436/86 |
| 4,597,966 | 7/1986 | Zolton et al. | 424/85 |

FOREIGN PATENT DOCUMENTS

| | | |
|---|---|---|
| 1007568 | 3/1977 | Canada . |
| 1072444 | 2/1980 | Canada . |
| 1112166 | 11/1981 | Canada . |
| 1142175 | 3/1983 | Canada . |
| 1168152 | 5/1984 | Canada . |
| 1210329 | 8/1986 | Canada . |

OTHER PUBLICATIONS

Wang et al, Parent of Formulations of Protions and Peptides: Stability and Stabilizers, vol. 42, No. 25, pp. 5-12 (1988).

Surgenor et al; Preparation and Properties of Serum and Plasma Proteins, XXXV A System of Protein Fractionation Using Zinc Complexes, Vox Sang, 5:272-296 (1960).

*Primary Examiner*—F. T. Moezie
*Assistant Examiner*—Andrew G. Rozycki
*Attorney, Agent, or Firm*—Anthony J. DeLaurentis

[57] ABSTRACT

An immunoglobulin-rich fraction containing IgG, IgA and IgM is prepared in high concentration (200 mg/ml) by contacting diluted serum with $CuSO_4$, which is a source of strong positive ions, to produce a precipitate rich in immunoglobulins, whereafter the precipitate is washed with an EDTA chelating agent solution and then a solution of L-lysine.HCl and $NaHCO_3$ is added to form a colloidal solution of the washed immunoglobulin precipitate.

3 Claims, 5 Drawing Sheets

Double Immunodiffusion

CENTER WELL:
Affinity Purified Antibody to Horse IgG (H+L) 1 mg/ml

SAMPLE 1:
Immunoglobulin
$\frac{1}{100} \rightarrow \frac{1}{3200}$

SAMPLE 2:
Supernatant from 0.001M $CuSO_4$ ppt.
$\frac{1}{2} \rightarrow \frac{1}{64}$ SAMPLE 3:
Supernatant from 0.001M EDTA wool
$\frac{1}{2} \rightarrow \frac{1}{64}$ SDS Agar Gel Electrophoresis SAMPLES
A = Supernatant from 0.001 M $CuSO_4$ ppt.

B = Immunoglobulin $\frac{1}{100}$

C = Supernatant from 0.001 M EDTA wash

MAJOR BANDS:
26. Albumin
24. IgG
22. IgA
21. Fibrinogen
18. $\alpha_2$-Macroglobulin
17. IgM

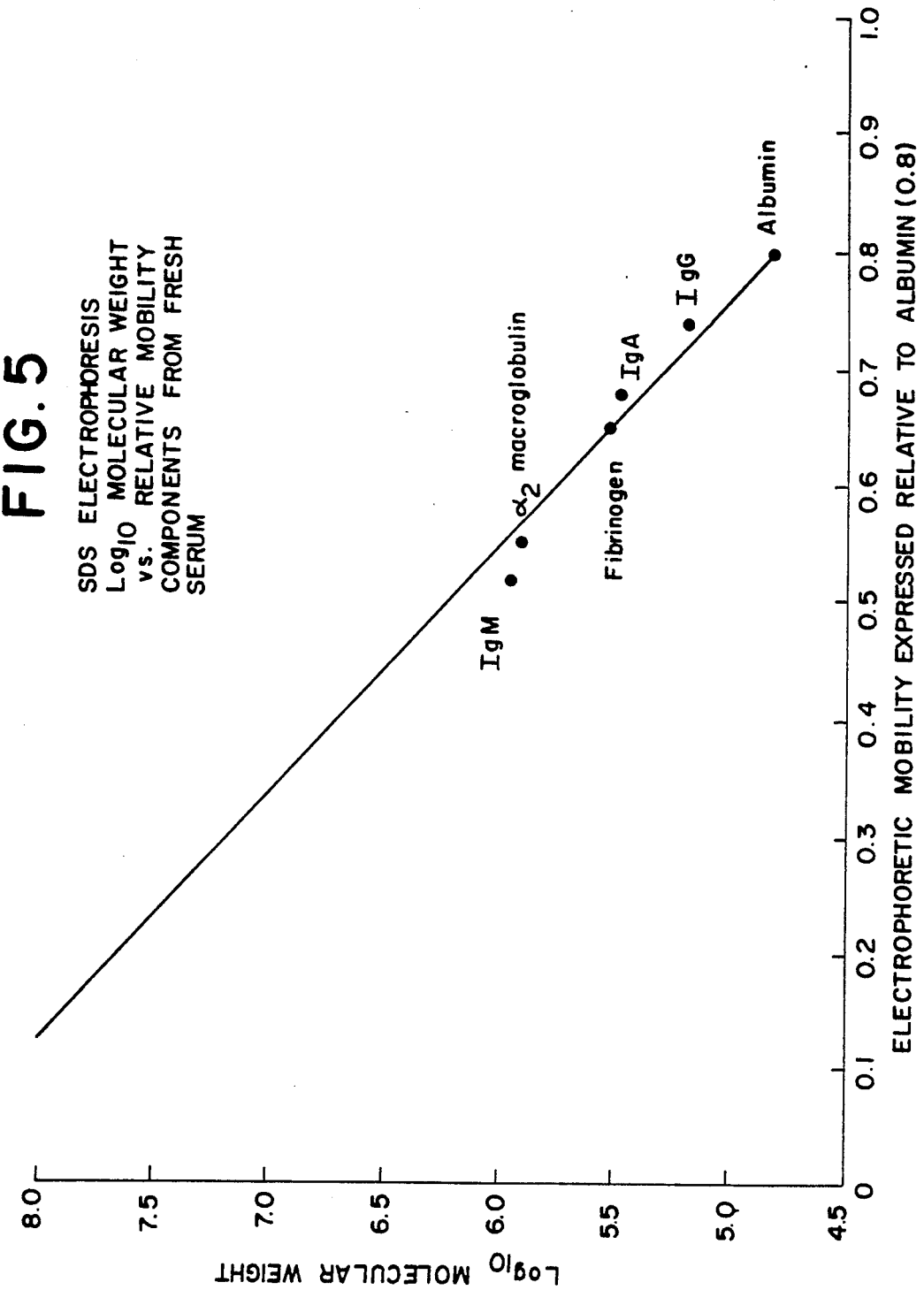

IMMUNOGLOBULIN EXTRACTION UTILIZING PROPERTIES OF COLLOIDAL SOLUTIONS

BACKGROUND

This invention relates to a process for the extraction of an undenatured immunoglobulin rich fraction from a fluid, such as serum, which contains immunoglobulins, and to the immunoglobulin rich fraction so extracted. More particularly the invention relates to a process for producing an undenatured immunoglobulin rich fraction containing IgG, IgA and IgM in relatively high concentration, e.g. about 200 mg/ml.

Presently available immunoglobulin preparations have proven to be disappointing in their effectiveness for therapeutic use, possibly due to the protein content thereof having been denatured during purification.

SUMMARY OF THE INVENTION

It has now been found, in accordance with the present invention, that the therapeutically effective undenatured immunoglobulin rich fraction can be extracted from a fluid, such as serum, which contains immunoglobulins, without specialized equipment and at a relatively low cost. Furthermore, it has been found that the extraction process of this invention can be carried out effectively at room temperature. The extraction process of the present invention can be accomplished, for example, by first titrating a diluted fluid sample, e.g. serum, with a solution containing strong positive ions, such as copper, silver or gold ions, to produce a precipitate. The precipitate is then separated from the supernatant, e.g. by conventional gravimetrical separation, and is washed with a chelating solution, such as, for example, 0.001 M ethylenediamine tetraacetic acid disodium salt (EDTA) solution. The washed precipitate is collected and then is dispersed in a suitable fluid medium having negative and positive ions sufficient to re-establish the bielectric layer of the extracted immunoglobulins and to bring about a colloidal solution. A buffer such as 0.15 M lysine.HCl and 0.075 M $NaHCO_3$ generally is added to form the colloidal solution, the final immunoglobulin concentration of which is generally from about 100 to about 200 mg/ml. The present process is carried out in standard test tubes and laboratory equipment, generally at room temperature, and usually results in an undenatured immunoglobulin yield of at least about 6, for example from about 4 to about 8, typically about 6.5 g/l of serum.

DESCRIPTION OF THE DRAWINGS

FIG. 5 is a graphical representation of the relative mobilities of the components in the Samples A, B and C of the SDS agar gel electrophoresis shown in FIG. 4 as a linear function of their respective log 10 molecular weights.

DETAILED DESCRIPTION

Figure 1:
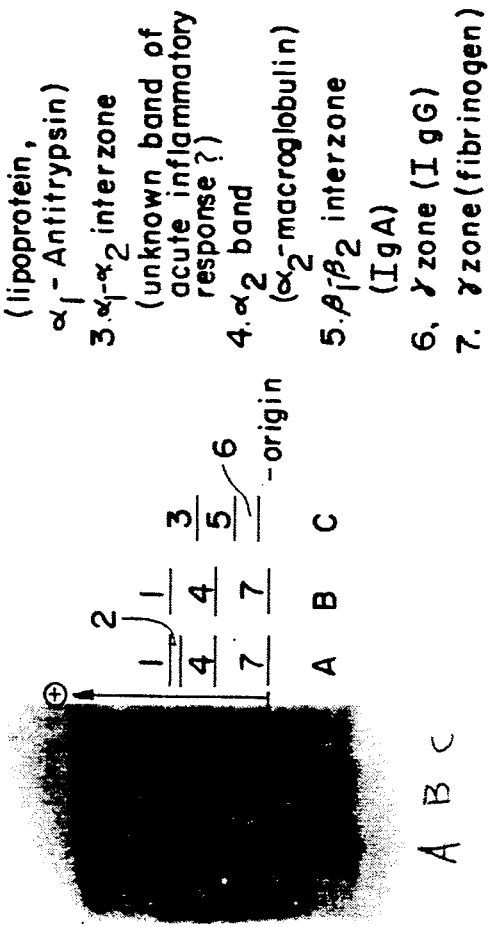
FIG. 1 is a photographic plate, with accompanying description, of an agar gel electrophoresis of the supernatant from the precipitation step for a sample of never frozen horse serum (Sample A), of the supernatant from the wash step (Sample B), and of the buffered immunoglobulin product (Sample C) prepared in accordance with the process of the present invention.

The immunoglobulin extraction process in accordance with the present invention is most easily explained with reference to theories relating to properties of colloidal solutions. In this regard, colloids are thought to remain suspended in solution partly due to mutual repulsion of like charges. Organic colloids usually possess a negative charge. A negatively charged colloid is thought to derive its charge from a layer of closely held negative ions. Next to this layer of negative ions is a loosely held outer layer of positively charged ions. This arrangement is referred to as a "bielectric layer". Thus, on the basis of mutual repulsion, it can be speculated that a charged water soluble protein, such as albumin, would tend to keep less soluble colloids in suspension by mutual repulsion.

A major principle of the present separation lies in the manipulation of these forces of repulsion created by the electric fields o the various charged ions in solution. For an individual ion the electric field varies directly with its mass and charge. The strength of this field is inversely proportional to the distance from the charged mass. The mutual repulsion experienced by the various components in a fluid sample, such as serum, is thus a function of their respective masses and charges as well as their distance from one another which is a function of the relative dilution of the sample.

The flocculation of a colloidal solution can be caused by the addition of strong ions into the fluid system. For example, the addition of strong positive ions, such as, for example, copper ($Cu^{++}$), silver ($Ag^+$), or gold ($Au^{+3}$), to a solution of negatively charged colloids, for example, organic colloids, causes the attraction of negative ions away from the closely held inner bielectric layer of the colloid to the strongly charged positive ions. The colloidal particles become less repulsed and tend to aggregate and flocculate from solution. This effect can be enhanced by heating the solution to produce increased Brownian motion and the probability of subsequent collisions between colloidal particles.

In one preferred embodiment of the present invention, the above theories relating to colloidal solutions are utilized in the extraction of immunoglobulin from serum, such as horse serum or cow serum. Such utilization requires the dilution of a serum sample with water or other suitable diluent, followed by titration of the diluted serum with a solution containing a strong positive ion concentration. Careful titration is required with respect to serum as it becomes readily apparent that large amounts of precipitate, of predominantly lipoid nature, can result. Fortunately, there is a serum dilution and strong ion concentration at which the precipitate forms quickly and settles rapidly i.e. richer in protein than lipoid material, and is primarily immunoglobulin. For example, with horse serum this point occurs at approximately a 1 in 8 dilution with water and an approximately 0.001 molar (M) cupric sulphate ($CuSO_4$) concentration. With cow serum this point occurs at approximately a 1 in 4 dilution with water and an approximately 0.001 M $CuSO_4$ concentration or at approximately a 1 in 8 dilution with water and an approximately 0.0005 M $CuSO_4$ concentration, but the latter appears to contain more lipoid material. It will be appreciated, of course, that the concentration of components of the serum may vary over relatively wide limits, and that the concentration and the identity of the strong positive ions might vary as well. For example, suitable serum dilutions can vary from about 1 part serum to about 1 to 32 parts water (by volume), typically from about 1 part serum to about 2 to 16 parts water, and preferrably from about 1 part serum to about 4 to 8 parts water. The strong ion concentration may vary from about 0.0002M to about 0.008M (molar), typically from about 0.0004 to about 0.004 M and preferrably from about 0.0005M to about 0.001 M. Suitable strong positive ions include, for example, $Cu^{++}$, $Ag^+$, $Au^{+++}$, and mixtures thereof. In the most preferred embodiments, the strong positive ion is $Cu^{++}$, which may be added to the diluted serum in the form of a solution of cupric sulfate, cupric chloride or the like.

The temperature at which the serum is titrated may vary over a relatively wide range, for example, ranging on the order of from about $-7°$ C. to about $45°$ C., and typically from about $20°$ C. to about $30°$ C. However, it has been found that lowering the titration temperature lowers the yield of immunoglobulin. Therefore, the titration step generally is carried out at about room temperature (25 degrees centigrade (C)). After thorough mixing, the titrated serum is left to run to completion, often overnight. It has been found that the solution of the strong positive ions which is added to the diluted serum, e.g. an aqueous $CuSO_4$ solution at 0.001 M concentration, seems to possess some antiseptic properties in the sense of keeping the titrated serum relatively free of contaminants in the absence of any additional aseptic treatment.

The precipitate which is formed in the above titration is separated from the supernatant, usually by aspiration of supernatant after a predetermined settling period, e.g. overnight. The precipitate is rich in strong positive ions, e.g. copper ions.

To remove these ions, as well as any water soluble proteins trapped in the precipitate, a large volume of water wash containing a chelating agent such as ethylenediamine tetraacetic acid disodium salt (EDTA), penicillamine or the like is used. The use of small wash volumes at this step tends to result in large losses of product. While the reason for such product loss when using small wash volumes is not completely understood, the loss is likely due to neutralization of the strong electric field of the strong positive ions through bonding with the chelating agent and the re-establishment of the organic colloid repulsion field by albumin. When large wash volumes are used, for example, typically from about 4 to 10 times the original serum volume, the repulsion field is weak and albumin being water soluble is carried away in the wash. Also, the lipid content of the precipitate appears to be reduced further. With respect to horse serum and cow serum extractions, it has been found that one ethylenediamine tetraacetic acid disodium salt (EDTA) wash having a concentration on the order of from about 0.0005 to about 0.0015 M EDTA was sufficient at a volume equal to that of the extraction (titration) step. The precipitate slurry from the extraction step is transferred to the chelating agent wash, and after thorough mixing, the wash is left to run to completion, often overnight. The use of water alone as a wash is not very effective in lowering the strong positive ion concentration or decreasing lipoid content and, therefore, it is less preferred. The precipitate slurry from the wash step is collected and centrifuged to concentrate the immunoglobulin-containing pellet. To dissolve the pellet, a compatible solution must be formulated. Most buffers have been found to be relatively ineffective for dissolving the pellet; rather, most buffers tend toward the formation of aggregates which is an annoying problem.

In a study of low temperature $(-7°$ C.) precipitation of immunoglobulins from diluted serum, it was observed that such immunoglobulins could be added back to serum in concentrations of about 100–200 mg/ml without the aggregation problem; furthermore, there was an increase in pH of the serum and immunoglobulin solution. This indicated that the $H^+$ ion concentration had decreased with respect t the $OH^-$ ion concentration. Although the reasons for these observations are not completely understood, it would appear to follow that serum proteins possessing $H^+$ions, e.g. lysine residues, arginine residues or the like, could be involved in the solution process of these cryoprecipitated immunoglobulins. By titration it was observed that the solution process could be performed equally well with a 0.4 M L-lysine monohydrochloride (L-lysine.HCl) solution as with the serum. This effect is probably due to repulsion between lysine molecules and the positive ions of the outer bielectric layer of the immunoglobulin, which may now be partly made up of lysine molecules also. By adding negatively charged ions, e.g. bicarbonate ion ($HCO_3^-$), to the solution to build up the inner bielectric layer, it was found that the concentration of positive ions, e.g. lysine, could be reduced. For example, it was found that L-lysine.HCl could be reduced to 0.15 M at a sodium bicarbonate ($NaHCO_3$) concentration of 0.075 M. This observation tends to support further the existence of a bielectric layer about the immunoglobulin and thus its colloidal nature. Also, it was found that a solution could be formulated from negative ions only, e.g. $NaHCO_3$ at 0.4 M. Therefore, the formulation of the solution should be determined empirically with respect to a particular application. For example, for injection, a solution closer to isotonic, e.g. 0.15 M L-lysine.HCl and 0.075 M $NaHCO_3$, could be suitable; whereas, for other applications, which require a neutral pH, a 0.4 M L-lysine.HCl solution could be used. Generally speaking, a solution containing L-lysine.HCl and $NaHCO_3$ (at a concentration on the order of about 0.1 to 0.2 M and 0.05 to 0.10 M, respectively, typically about 0.15 M and 0.075 M, respectively,) is used since it results in a solution which has a pH close to 8.6 and which performs well in separations such as electrophoresis (FIG. 1), double immunodiffusion (FIG. 3) or chromatography. Also, based on this solution, sodium dodecyl sulphate (SDS) agarose electrophoresis molecular weight separations are possible (FIGS. 4 and 5). Referring more specifically to FIG. 1, there is shown a photograph of the results of a 0.8% agar gel electrophoresis separation (70 volts, 35 mA, 1 hour) of the supernatant recovered from the extraction (precipitation) step of a sample of never frozen horse serum which was diluted 1 part serum in 8 parts water and a final $CuSO_4$ concentration of 0.001M (Sample A). Also shown (Samples B and C, respectively) are the results of the electrophoresis of the supernatant recovered from a large volume wash, e.g. one 900 ml volume of wash water having an EDTA concentration of 0.001 M; and the results of the electrophoresis of the immunoglobulin-containing washed precipitate diluted 1 in 100 with 0.15 M L-lysine.HCl, and 0.075 M NaHCO$_3$. As shown in FIG. 1, there was very little cathodal migration in the gamma ($\gamma$) zone (low electroendosmosis effect) and the albumin band was just able to be discerned from the alpha$_1$ ($\alpha_1$) band. The major bands which were identified for the supernatant of the precipitation step (Sample A) are an albumin band, a $\alpha_1$ band (lipoprotein, $\alpha_1$-antitrypsin), a $\alpha_2$ band ($\alpha_2$-macroglobulin), and a $\gamma$ zone (fibronogen). The major bands which were identified for supernatant from the large volume wash (Sample B), are the albumin, a$\alpha_2$ and $\gamma$ zones identified in connection with Sample A; and the major bands identified for the diluted immunoglobulin product (Sample C) are an $\alpha_1$-$\alpha_2$ interzone (unknown band of acute inflammatory response), a $\beta_1$-$\beta_2$ interzone (IgA) and a $\gamma$ zone (IgG). Note: IgM is usually found near the origin in the $\gamma$ zone.

Figure 2:
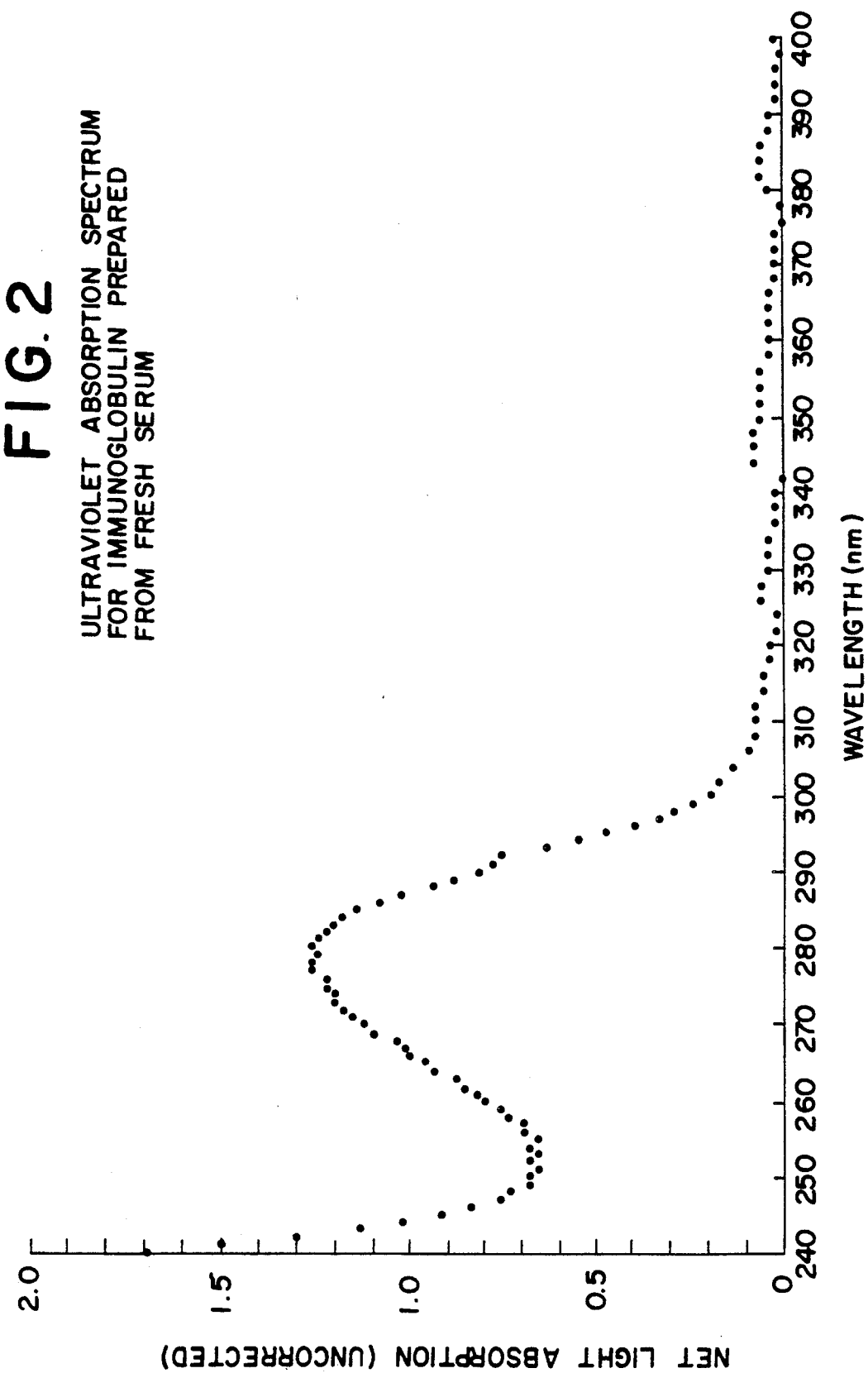
FIG. 2 is a graphical representation of an ultraviolet absorption spectrum from 240 nm to 400 nm for the immunoglobulin product prepared from never frozen serum using the present process.

FIG. 2 illustrates the ultraviolet absorption spectrum for the immunoglobulin product (Sample C) prepared from fresh never frozen serum in accordance with the process outlined above in connection with FIG. 1. The spectrum is illustrated in terms of net light absorbed (uncorrected) versus wavelength between 240 and 400 nm.

Figure 3:
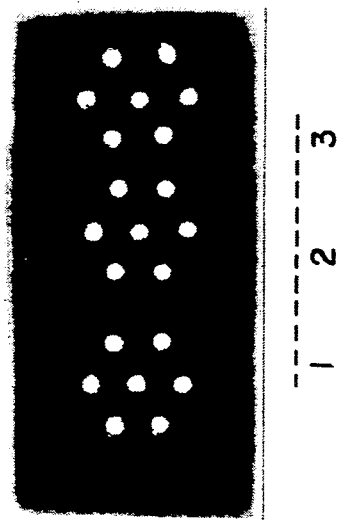
FIG. 3 is a photograph and accompanying description of double immunodiffusion of steps in the extraction of the immunoglobulin product prepared in accordance with the present invention.
Figure 4:
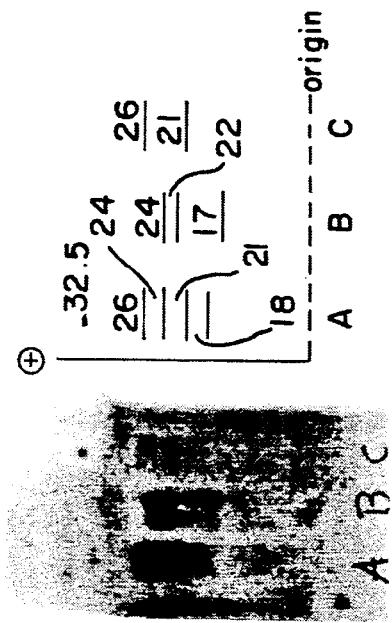
FIG. 4 is a photograph and accompanying description of an SDS agar gel electrophoresis similar to FIG. 1.

FIG. 3 illustrates the results of a double immunodiffusion at various stages of the immunoglobulin extraction from never frozen horse serum in accordance with the present invention. As shown in FIG. 3, Sample 1 is the immunoglobulin product diluted 1 in 100 to 1 in 3200, Sample 2 is the supernatant from the 0.001 M CuSO$_4$ precipitation step diluted 1 in 2 to 1 in 64, and Sample 3 is the supernatant from large volume 0.001 M EDTA wash diluted 1 in 2 to 1 in 64. The center well in each case contained affinity- purified antibody to horse IgG (H+L). The gel was 1.0% agar in 0.15 M L-lysine.HCl, 0.075 M NaHCO$_3$ with 0.01% thimerosal as preservative. The samples were diluted with a solution of 0.15 M L-lysine.HCl and 0.075 M NaHCO$_3$.

FIG. 4 is a photographic plate, similar to FIG. 1, illustrating the results of a sodium dodecyl sulfate (SDS) agar gel electrophoresis separation (70 volts, 30 mA, 1 hour) of the supernatant from the 0.001 M CuSO$_4$ precipitation step (Sample A), the immunoglobulin-containing washed precipitate diluted 1 in 100 with 0.15 M L-lysine.HCl, 0.075 M NaHCO$_3$ and 0.1% sodium dodecyl sulfate (Sample B), and the supernatant from the large volume 0.001 M EDTA wash (Sample C). The samples were prepared in 2% SDS and electrophoresis solution before application to the gel. Sample A and Sample C were diluted 1 in 1 with electrophoresis solution and Sample B was diluted 1 in 100 with the same electrophoresis solution. The electrophoresis solution was a 0.15 M L-lysine.HCl, 0.075 M NaHCO$_3$ and 0.1% SDS solution. The gel was 0.8% agar.

As can be seen, FIG. 4 shows almost no evidence of aggregate bands between the position of the IgM band and the origin. The major bands identified for the supernatant from the precipitation step (Sample A) are an albumin band, an IgG band, a fibrinogen band, and an $\alpha_2$-macroglobulin band. The major bands identified for the diluted, washed immunoglobulin product (Sample B) are an IgG band, an IgA band, and IgM band. The major bands identified for the supernatant from the large volume EDTA wash (Sample C) are an albumin band and a fibrinogen band.

FIG. 5 graphically depicts the relative mobilities of the components within Samples A, B and C of the SDS agar gel electrophoresis illustrated in FIG. 4 as a linear function of their respective log 10 molecular weights.

In connection with the agar gel electrophoresis and the immunodiffusion illustrated in FIGS. 1, 3 and 4, the agar gel was stained using an aqueous solution containing 47.5% (v/v) ethyl alcohol, 2.5% (v/v) acetic acid, and 0.03% (w/v) Coomassie ® Brilliant Blue. At completion of the respective electrophoresis or immunodiffusion separations, the gel was placed immediately in the above stain. The fixing and staining steps took place at the same time over a period of several hours. After fixation and staining, the gels were transferred to a destaining bath. Usually several changes of water over several hours or a few days are successful in decreasing background stain and removing buffer salts from the gel. Finally, after the gels were sufficiently destained, they were left to dry on their respective glass slides at room temperature.

When practicing the invention as outlined above, one liter of horse serum generally yielded 6 or more grams, typically about 6.5 grams (dry weight) of immunoglobulin-rich fraction at a final concentration of about 200 mg per ml of 0.15 M L-lysine.HCl, 0.075 M NaHCO$_3$ solution, and a strong positive ion, e.g. copper ion, concentration of about 5 mg/l. As discussed above in connection with FIGS. 1, 3, 4 and 5, the immunoglobulin-rich fraction appears to contain IgG, IgA and IgM.

Ultraviolet spectroscopy of the final product revealed that immunoglobulin is very sensitive to its physical environment. FIG. 2 illustrates a typical ultraviolet absorption spectrum for the immunoglobulin-rich fraction that was prepared from freshly prepared horse serum in the manner described in connection with FIG. 1. When an immunoglobulin-rich fraction prepared from a thawed sample of frozen horse serum is analysed the absorption peak around 277 nanometers (nm) tends to be higher and broader and the minor absorption peaks above 300 nm are also higher. The chromophores tryptophan, tyrosine and phenylalanine are largely responsible for the 277 nm peak, and the conjugation of double bonds are largely responsible for the weak absorption peaks above 300 nm (FIG. 2). Also, the immunoglobulin fraction prepared from thawed serum contains a richness of aggregates, which can be visualized by electrophoretic techniques, which are more scarce in the fraction prepared from fresh never frozen serum. It is then possible that the increased absorption peak at 277 nm is due partly to increased separation of the chromophores, e.g. denatured due to freezing and/or the formation of aggregates stabilized by conjugate bonding between molecules. New stabilized conjugate bonding within the denatured molecule, as well as molecular aggregation, are likely responsible for the increased absorption over 300 nm. These observations would suggest that freezing temperatures should be avoided in the preparation and storage of the immunoglobulin fraction. Based on the dry weight of the immunoglobulin-rich fraction prepared in accordance with this invention, and its absorbance of ultraviolet light at 277 nm, an extinction coefficient of 10.4 was calculated for a 10 mg/ml solution of horse immunoglobulin. This value is comparable to those reported for IgM, an immunoglobulin typically prepared by dilution instead of salt or alcohol precipitation. It would then appear that previous immunoglobulin precipitation techniques affect the structure of the immunoglobulin molecules, e.g. IgG and IgA, as revealed by increased absorption of ultraviolet light.

Thus, it would appear evident that immunoglobulin extraction in accordance with the present invention, while utilizing the properties of colloidal solutions, offers many advantages over prior methods. Immunoglobulins presently employed in the therapy of immunodeficient states suffer from many problems, not the least of which are low effectiveness, low concentration and aggregates in the product. Immunoglobulins prepared by the herein described inventive process are relatively free of aggregates (FIGS. 4 and 5), thus negating the need for filter needles presently used to remove the larger aggregates. Moreover, the immunoglobulins prepared in accordance with the process of this invention are of high concentration, e.g. 200 mg/ml, and appear to include structural differences which could prove this product to be more biologically active and closer in nature to the circulating immunoglobulin in vivo than immunoglobulin products in current use. It is also noted that opportunistic contamination appears to be inhibited in the immunoglobulin product prepared by the process of the present invention.

The present invention will be appreciated more fully when viewed in conjunction with the following examples.

EXAMPLE 1

A 100 ml sample of fresh, never frozen horse serum was diluted in a one liter bottle at room temperature (25° C.) in 791 ml of deionized water, whereafter 9 ml of 0.1M $CuSO_4$ solution was added to give a final diluted $Cu^{++}$ ion concentration of approximately 0.001M. It was found that the order of solution was not critical, i.e. essentially the same results were achieved regardless of whether a dilute copper sulfate solution were added to the serum, or a concentrated copper sulfate solution were added to the serum followed by dilution with water, or the serum were first diluted with water followed by the addition of a copper sulfate solution. The dilution of the serum and the addition of the copper sulfate thereto, regardless of the order of addition and dilution, resulted in an oatmeal-like precipitate which settled relatively quickly.

The contents of the bottle were allowed to stand overnight, whereafter the supernatant was separated from the precipitate. The precipitate was washed in 900 ml of a 0.001 M aqueous solution of EDTA and the wash fluid/precipitant mixture was allowed to stand overnight.

The resulting supernatant and precipitate were separated, the precipitate then being collected and centrifuged at high speed in a clinical centrifuge. The remaining supernatant was separated from the centrifuged pellet. The pellet, volume between 1.5 and 2.0 ml, was then diluted with 1.5 ml of an aqueous buffer solution containing 0.30 M L-lysine.HCl and 0.15 M $NaHCO_3$ to give an approximate final concentration of 0.15 M L-lysine and 0.075 M $NaHCO_3$ when mixed with the pellet and trapped wash solution to re-establish the bielectric layer of the immunoglobulin in the precipitate and to bring about a colloidal solution. The final concentration of the colloidal solution was adjusted to about 200 mg/ml. The colloidal solution was analyzed by agar gel electrophoresis (0.8% agar gel, 70 volts, 35 mA, 1 hour) using an electrophoresis solution comprising 0.15 M L-lysine.HCl and 0.075 M $NaHCO_3$. The major bands observed as a result of the electrophoresis indicated the presence in the colloidal solutions of IgA ($\beta_1-\beta_2$ interzone) and IgG ($\gamma$ zone). It is also noted that IgM migrates in the gamma zone near the origin.

An $\alpha_1-\alpha_2$ zone (unknown band of acute inflammatory response) was also observed.

EXAMPLE 2

A 5 ml sample of horse serum was diluted in 39.2 ml deionized water in a 50 ml centrifuge tube and to this was added 1.2 ml of 0.5% auric trichloride ($AuCl_3$) solution to produce a final diluted $Au^{+++}$ ion concentration of about 0.0004M. The precipitate was left to form and settle out overnight. The supernatant and the precipitate were separated and the precipitate was washed by mixing it with 40 ml of 0.001M penicillamine solution. The precipitate was once more allowed to settle overnight. The supernatant wash was separated from the precipitate and the precipitate plus remaining wash was centrifuged at high speed in a clinical centrifuge. The supernatant was removed and the pellet was resuspended in 1 ml of 0.4M L-arginine.HCl. The entire process was carried out at room temperature (about 25° C). Aqueous solutions of penicillamine prepared for the wash step tend to form precipitates on standing and thus should be used shortly after preparation. A small amount of similar precipitate formed in the final product and was removed by centrifugation. Relatively little penicillamine-like precipitate formed afterwards. It has been reported that penicillamine solutions are relatively stable at pH 2-4. In vivo acidic pH requirements may be met at neutral pH by positively charged amino acids such as L-arginine or L-lysine. Samples of the supernatant from the 0.0004M $Au^{+++}$ precipitation step, the 0.001M penicillamine wash step and the colloidal solution of IgG were analysed by electrophoresis using 0.8% agar gel, 70 volts, and 35 mA for 1 hour with a 0.15M L-lysine.HCl and 0.075M $NaHCO_3$ electrophoresis solution. The results of the elecrophoresis were similar to those obtained using $CuSO_4$, EDTA and 0.15M L-lysine.HCl with 0.075M $NaHCO_3$. The yield of immunoglobulins was approximately 50 percent lower than that obtained using the method described in Example 1.

EXAMPLE 3

Solutions containing positive and/or negative ions of sufficient charge to form a colloidal suspension of immunoglobulins can be formulated. At present the criterion for sufficient charge is determined empirically. For example, L-arginine.HCl is positively charged at neutral pH as was L-lysine.HCl in the previous example. Serial dilutions were prepared of L-arginine.HCl as follows: 0.4, 0.2, 0.1 and 0.05 M. A 100 ml sample of horse serum was processed according to the procedure set forth in Example 1 until the end of the EDTA wash step. At this point the precipitate was slurried (total volume approximately 80 ml) and 10 ml volumes were aliquoted to each of four labelled centrifuge tubes. The precipitates were concentrated in pellets by centrifugation and the supernatants discarded. A two ml volume of each L-arginine.HCl dilution was pipetted into its respective centrifuge tube and mixed well with the pellet therein. It was observed that L-arginine.HCl at a concentration of 0.4 M changed the immunoglobulins from a precipitate to colloidal particles in a solution. It was not as effective at the other concentrations.

EXAMPLE 4

A cell culture medium was formulated to possess an immunoglobulin carrying capacity comparable to serum with the view that it would be useful in the culture of mono- or poly-clonal antibody producing cells. It was based on a solution of L-lysine.HCl and NaHCO$_3$ with the addition of essential amino acids, vitamins and glucose, the NaHCO$_3$ being added in the final step as a 5.6% solution to adjust the pH to approximately 7.4 as indicated by phenol red (17 mg/l) incorporated in the medium formulation. The final medium contained approximately 0.15 L-lysine.HCl and 0.024 M NaHCO$_3$ plus essential amino acids, vitamins and glucose for cellular metabolism i.e. minimum essential medium (MEM) formulated by H. Eagle, Science 130:432-437 (1959). This modified MEM was used to establish and maintain a primary cell culture without the use of serum supplementation. Primary cell cultures of murine thymocytes, mechanically dissociated using a 70 μm nylon mesh, were initiated in plastic tissue culture flasks, 25 cm$^2$, and maintained at 37° C. with medium changes about every other day. At 10 days and 30 days in vitro the cells were fixed in formaldehyde, stained with methylene blue and air dried. Three main types of cells were observed under a low power light microscope. At 10 days small round cells were observed randomly distributed over the surface of the flask and were likely lymphocytes. There were also a few localized areas which contained cells that resembled fibroblasts. At 30 days the small round lymphocyte cell type still predominated. In localized areas there were now small cells with long slender processes which appeared to interconnect to form networks over 1.0 mm in length. These cells were probably reticular cells. Also observed in the 30 day cultures were scattered and independent polymorphic "giant" cells, which often extended over 0.5 mm. These cells were probably macrophages which differentiated form small precursor cells.

Immunoglobulins are used in the treatment of immunodeficient states which occur in a wide variety of instances ranging from disease processes, e.g. AIDS, to situational factors, e.g. space flight. Furthermore, the incorporation of sufficient concentration of L-lysine.HCl and sodium bicarbonate into the cell culture medium of the mono- or polyclonal antibody producing cell lines should increase the potential concentration level of antibody in the supernatant. Thus, when a cell culture medium was formulated using 0.15 M L-lysine.HCl and 0.024 M NaHCO$_3$, plus essential amino acids, vitamins and glucose, and with respect to a primary cell culture of murine thymocytes (30 days in vitro), it was found that this medium required no serum supplementation and was autoclavable (NaHCO$_3$ autoclaved separately and added as the final pH adjustment step ). Presently available cell culture media generally require the addition of serum except in the case of some established cell lines, and are usually sterilized using more expensive filtration techniques. Also, the problem of cryoprecipitate formation in refrigerated blood, plasma and serum could be prevented by the addition of sufficient L-lysine.HCl and sodium bicarbonate. Another use to which the buffer solution prepared in accordance with the present invention may be put include, for example, use as a bath for reducing the formation of immunoglobulin aggregates on tissues and organs for transplant. The present process may be facilitated by the use of a kit which contains the appropriate calibrated dilution vessels, pipettes and solutions of, for example, cupric sulfate, EDTA, L-lysine.HCl, and sodium bicarbonate in concentrations appropriate to the volume of the dilution vessels as a means for diluting, precipitating and washing the immunoglobulins and for re-establishing the precipitated immunoglobulins as a colloidal solution.

The disclosure and examples contained herein are intended to be illustrative of the process of extracting immunoglobulin and its subsequent rendering into a useful form and are not meant to be taken as limiting. To those skilled in the art many applications which possess the spirit of this invention will be obvious in view of the appended claims.

What is claimed is:

1. A process for extracting undenatured immunoglobulins from a water soluble precipitate containing EDTA-insoluble undenatured immunoglobulins and EDTA-soluble lipoid material, which consists essentially of:
   (a) washing the water insoluble precipitate with a solution of EDTA to remove lipoid material therefrom; and
   (b) rendering the resulting essentially lipoid material-free undenatured immunoglobulins-containing precipitate into colloidal suspensions in a fluid system comprising:
      (i) a source of positive ions selected from the group consisting of L-lysine.HCl, L-arginine.HCl, and mixtures thereof; and
      (ii) sodium bicarbonate as a source of negative ions.

2. A process for extracting undenatured immunoglobulins from a fluid system containing undenatured immunoglobulins, consisting essentially of:
   (a) diluting the fluid system containing the undenatured immunoglobulins;
   (b) adding to the fluid system containing the undenatured immunoglobulins copper ions to flocculate undenatured immunoglobulins to produce a precipitate containing undenatured immunoglobulins which are essentially insoluble in EDTA steps, (a) and (b) being performed in any order and being titrated to maximize protein material content and to minimize lipoid material content in said precipitate;
   (c) after completion of the flocculation step (b), separating said precipitate from the supernatant liquid; washing said precipitate with an EDTA solution to remove any lipoid material therefrom and to chelate the copper present therein; and
   (e) rendering the essentially lipoid material-free precipitate containing undenatured immunoglobulins into a colloidal suspension in a fluid system comprising:
      (i) a source of positive ions selected from the group consisting of L-lysine.HCl, L-arginine.HCl, and mixtures thereof; and
      (ii) sodium bicarbonate as a source of negative ions.

3. The process according to claim 2, wherein CuSO$_4$ is the source of said copper ions added to step (b).

* * * * *